United States Patent
Marom et al.

(10) Patent No.: US 9,200,114 B2
(45) Date of Patent: Dec. 1, 2015

(54) RANDOM PENTAPOLYMER FOR TREATMENT OF AUTOIMMUNE DISEASES

(71) Applicant: MAPI PHARMA LTD., Ness Ziona (IL)

(72) Inventors: Ehud Marom, Kfar Saba (IL); Shai Rubnov, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 13/764,460

(22) Filed: Feb. 11, 2013

(65) Prior Publication Data

US 2013/0156725 A1 Jun. 20, 2013

Related U.S. Application Data

(63) Continuation of application No. PCT/IL2012/050138, filed on Apr. 16, 2012.

(60) Provisional application No. 61/477,610, filed on Apr. 21, 2011.

(51) Int. Cl.
| | | |
|---|---|---|
| A61K 38/02 | (2006.01) | |
| A61K 38/16 | (2006.01) | |
| C08G 69/10 | (2006.01) | |
| C07K 14/00 | (2006.01) | |
| A61K 31/785 | (2006.01) | |
| A61K 45/06 | (2006.01) | |
| A61K 38/00 | (2006.01) | |

(52) U.S. Cl.
CPC .............. *C08G 69/10* (2013.01); *A61K 31/785* (2013.01); *A61K 45/06* (2013.01); *C07K 14/001* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,773,919 A | 11/1973 | Boswell et al. | |
| 3,845,770 A | 11/1974 | Theeuwes et al. | |
| 3,849,550 A | 11/1974 | Teitelbaum et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,578,442 A | 11/1996 | Desai et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,559 A | 3/1998 | Citernesi | |
| 5,800,808 A | 9/1998 | Konfino et al. | |
| 5,858,964 A | 1/1999 | Aharoni et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,214,791 B1 | 4/2001 | Arnon et al. | |
| 6,342,476 B1 | 1/2002 | Konfino et al. | |
| 6,362,161 B1 | 3/2002 | Konfino et al. | |
| 6,514,938 B1 * | 2/2003 | Gad et al. ........................ 514/1.1 |
| 6,620,847 B2 | 9/2003 | Konfino et al. | |
| 6,835,711 B2 | 12/2004 | Eisenbach-Schwartz et al. | |
| 6,844,314 B2 | 1/2005 | Eisenbach-Schwartz et al. | |
| 6,939,539 B2 | 9/2005 | Konfino et al. | |
| 7,195,778 B2 | 3/2007 | Fleshner-Barak et al. | |
| 7,199,098 B2 | 4/2007 | Konfino et al. | |
| 7,230,085 B2 | 6/2007 | Griffiths et al. | |
| 7,351,686 B2 | 4/2008 | Eisenbach-Schwartz et al. | |
| 7,381,790 B2 | 6/2008 | Strominger et al. | |
| 7,576,051 B2 | 8/2009 | Kurokawa et al. | |
| 7,655,221 B2 * | 2/2010 | Rasmussen et al. ........ 424/78.08 |
| 8,138,201 B2 | 3/2012 | Kalafer | |
| 8,377,885 B2 * | 2/2013 | Marom et al. ................ 514/17.9 |
| 2002/0037848 A1 | 3/2002 | Eisenbach-Schwartz et al. | |
| 2004/0038887 A1 | 2/2004 | Strominger et al. | |
| 2005/0170005 A1 | 8/2005 | Rashba-Step et al. | |
| 2006/0189527 A1 | 8/2006 | Rasmussen et al. | |
| 2006/0264354 A1 | 11/2006 | Aharoni et al. | |
| 2006/0276390 A1 | 12/2006 | Aharoni et al. | |
| 2007/0021341 A1 | 1/2007 | Sela et al. | |
| 2007/0081976 A1 | 4/2007 | Cohen et al. | |
| 2007/0248569 A1 | 10/2007 | Eisenbach-Schwartz et al. | |
| 2008/0063687 A1 | 3/2008 | Chou | |
| 2008/0085269 A1 | 4/2008 | Eisenbach-Schwartz et al. | |

(Continued)

FOREIGN PATENT DOCUMENTS

| | | |
|---|---|---|
| EP | 1799703 | 6/2007 |
| JP | 2007-500693 A | 1/2007 |

(Continued)

OTHER PUBLICATIONS

Abramsky O. et al., Alpha-fetoprotein suppresses experimental allergic encephalomyelitis. J Neuroimmunol. 1982;2(1):1-7.
Aharoni et al., Bystander suppression of experimental autoimmune encephalomyelitis by T cell lines and clones of the Th2 type induced by copolymer 1. J. Neuroimmunol. 1998;91(1-2):135-46.
Aharoni R. et al., The immunomodulator glatiramer acetate augments the expression of neurotrophic factors in brains of experimental autoimmune encephalomyelitis mice. PNAS 2005; 102(52):19045-50.
Armstrong et al., (1997) A novel synthesis of disubstituted ureas using titanium(IV) isopropoxide and sodium borohydride. Tetrahedron Letters 38(9): 1531-1532.
Artuso et al., (2007) Preparation of Mono-, Di-, and Trisubstituted Ureas by Carbonylation of Aliphatic Amines with S,S-Dimethyl Dithiocarbonate. Synthesis 2007(22): 3497-3506.

(Continued)

*Primary Examiner* — Karlheinz R Skowronek
*Assistant Examiner* — Joseph Fischer
(74) *Attorney, Agent, or Firm* — Rothwell, Figg, Ernst & Manbeck, P.C.

(57) ABSTRACT

The present invention relates to a synthetic polypeptide which is a random linear pentapolymer comprising alanine, glutamic acid, lysine, tyrosine and phenylalanine and use thereof in treating autoimmune diseases, in particular multiple sclerosis.

14 Claims, No Drawings

(56) References Cited

U.S. PATENT DOCUMENTS

| | | |
|---|---|---|
| 2008/0194462 A1 | 8/2008 | Wucherpfennig et al. |
| 2009/0130121 A1 | 5/2009 | Arnon et al. |
| 2009/0191173 A1 | 7/2009 | Eisenbach-Schwartz et al. |
| 2009/0237078 A1 | 9/2009 | Shriver et al. |
| 2010/0135953 A1 | 6/2010 | Eisenbach-Schwartz et al. |
| 2010/0226963 A1 | 9/2010 | Cooper et al. |
| 2010/0298227 A1 | 11/2010 | Aharoni et al. |
| 2012/0015891 A1 | 1/2012 | Marom et al. |
| 2012/0164229 A1 | 6/2012 | Marom et al. |

FOREIGN PATENT DOCUMENTS

| | | |
|---|---|---|
| JP | 2007-509981 A | 4/2007 |
| JP | 2007-517902 A | 7/2007 |
| JP | 2007-531701 A | 11/2007 |
| JP | 2009-515999 A | 4/2009 |
| WO | 95/31990 | 11/1995 |
| WO | 00/05250 | 2/2000 |
| WO | 00/27417 | 5/2000 |
| WO | 01/52878 | 7/2001 |
| WO | 01/93893 | 12/2001 |
| WO | 2005/009333 | 2/2005 |
| WO | 2005009333 A2 | 2/2005 |
| WO | 2005/035088 A2 | 4/2005 |
| WO | 2005035088 A2 | 4/2005 |
| WO | 2005/041933 A1 | 5/2005 |
| WO | 2005041933 A1 | 5/2005 |
| WO | 2005/070332 A1 | 8/2005 |
| WO | 2005070332 A1 | 8/2005 |
| WO | 2005085323 A2 | 9/2005 |
| WO | 2007/059342 A2 | 5/2007 |
| WO | 2008/075365 | 6/2008 |
| WO | 2009/040814 | 4/2009 |
| WO | 2009/063459 | 5/2009 |
| WO | 2010/011879 A2 | 1/2010 |

OTHER PUBLICATIONS

Ben-Nun et al., The autoimmune reactivity to myelin oligodendrocyte glycoprotein (MOG) in multiple sclerosis is potentially pathogenic: effect of copolymer 1 on MOG-induced disease. J. Neurol. 1996;243(Supl):S14-22.
Bolton C. et al., Immunosuppression by cyclosporin A of experimental allergic encephalomyelitis. J Neuro Sci 1982;56 (2-3):147-53.
Bornstein et al. 1990, Clinical trials of Cop 1 in multiple sclerosis, in Handbook of Multiple Sclerosis, ed. Cook S.D. Marcel Dekker, Inc., p. 469-480.
Bright et al., (1999) Tyrphostin B42 inhibits IL-12-induced tyrosine phosphorylation and activation of Janus kinase-2 and prevents experimental allergic encephalomyelitis. J Immunol 162(10): 6255-6262.
Cohen et al., (2007) Randomized, double-blind, dose-comparison study of glatiramer acetate in relapsing-remitting MS. Neurology 68(12): 939-944.
Fridkis-Hareli et al., Binding of random copolymers of three amino acids to class II MHC molecules. Int. Immunol. 1999;11(5):635-41.
Johnson et al., (1995) Copolymer 1 reduces relapse rate and improves disability in relapsing-remitting multiple sclerosis: results of a phase III multicenter, double-blind placebo-controlled trial. The Copolymer 1 Multiple Sclerosis Study Group. Neurology 45(7): 1268-1276.
Sela et al., Suppressive activity of Cop-1 in EAE and its Relevance to Multiple Sclerosis. Bull. Inst. Pasteur (Paris) 1990;88:303-314.
Shenoy et al., (2002) Poly(DL-lactide-co-glycolide) microporous microsphere-based depot formulation of a peptide-like antineoplastic agent. J Microencapsul 19(4): 523-535.
Sorensen PS. et al., Intravenous immunoglobulin G reduces MRI activity in relapsing multiple sclerosis. Neurology 1998;50(5):1273-81.
Stern et al., (2008) Amino acid copolymer-specific IL-10-secreting regulatory T cells that ameliorate autoimmune diseases in mice. Proc Natl Acad Sci U S A 105(13): 5172-5176.
Teitelbaum et al., (1973) Suppression by several synthetic polypeptides of experimental allergic encephalomyelitis induced in guinea pigs and rabbits with bovine and human basic encephalitogen. Eur J Immunol 3(5): 273-279.
Teitelbaum et al., Copolymer 1 inhibits chronic relapsing experimental allergic encephalomyelitis induced by proteolipid protein (PLP) peptides in mice and interferes with PLP-specific T cell responses. J. Neuroimmunol. 1996;64:209-17.
Teitelbaum et al., Specific inhibition of the T-cell response to myelin basic protein by the synthetic copolymer Cop 1. Proc. Natl. Acad. Sci. USA 1988;85(24):9724-8.
Teitelbaum et al., Suppression of experimental allergic encephalomyelitis by a synthetic polypeptide. Eur. J. Immunol. 1971;1(4):242-8.
Teitelbaum et al., Suppression of experimental allergic encephalomyelitis in Rhesus monkeys by a synthetic basic copolymer. Clin. Immunol. Immunopathol. 1974;3(2):256-62.
Teitelbaum et al., Suppression of experimental allergic encephalomyelitis in baboons by Cop 1. Israeli Med. Sci. 1977;13:1038.
Webb et al., Correlation between strain differences in susceptibility to experimental allergic encephalomyelitis and the immune response to encephalitogenic protein in inbred guinea pigs. Immunol. Commun. 1973;2(2):185-92.
Bouissou et al., (2006) The Influence of Surfactant on PLGA Microsphere Glass Transition and Water Sorption: Remodeling the Surface Morphology to Attenuate the Burst Release. Pharmaceutical Research 23(6): 1295-1305.
Brown, L.R.: "Commercial Challenges of Protein Drug Delivery," (2005) Expert Opinion on Drug Delivery, Informa Healthcare, GB 2(1): 29-42.
Goodson JM: Dental applications; in Langer LS, Wise DL (eds): Medical Applications of Controlled Release. Boca Raton, CRC Press, 1984, vol. 2, pp. 115-138.
Langer R.: "New Methods of Drug Delivery," (1990) Science, American Association for the Advancement of Science, US 249(4976): 1527-1533.
Aharoni et al., (2008) Demyelination arrest and remyelination induced by glatiramer acetate treatment of experimental autoimmune encephalomyelitis. Proc Natl Acad Sci USA 105(32): 11358-11363.
Fridkis-Hareli (2013) Design of Peptide Immunotherapies for MHC Class-II-Associated Autoimmune Disorders. Clin Dev Immunol. 2013: 826191, 9 pages.
Ruggieri et al., (2007) Glatiramer acetate in multiple sclerosis: a review. CNS Drug Rev 13(2): 178-191.
Sabatos-Peyton et al., (2010) Antigen-specific immunotherapy of autoimmune and allergic diseases. Curr Opin Immunol 22(5): 609-615.

* cited by examiner

RANDOM PENTAPOLYMER FOR TREATMENT OF AUTOIMMUNE DISEASES

CROSS REFERENCE TO RELATED APPLICATIONS

The present application is a continuation application of International Application No.: PCT/IL2012/050138, with an international filing date of Apr. 16, 2012, which claims priority to U.S. Patent Application No. 61/477,610 filed Apr. 21, 2011, which are incorporated herein in their entireties.

FIELD OF THE INVENTION

The present invention relates generally to a synthetic linear random pentapolymer comprising alanine, glutamic acid, lysine, tyrosine and phenylalanine and use thereof for treating autoimmune diseases, in particular multiple sclerosis.

BACKGROUND OF THE INVENTION

A high molecular weight synthetic basic random copolymer consisting of L-Alanine (L-Ala), L-Glutamic acid (L-Glu), L-Lysine (L-Lys) and L-Tyrosine (L-Tyr) residues in a molar ratio of about 6 parts L-Ala to 2 parts L-Glu to 4.5 parts L-Lys to 1 part L-Tyr, and having a molecular weight of 15,000-25,000, was first described in U.S. Pat. No. 3,849,550 as an agent for the treatment or prevention of experimental allergic encephalomyelitis (EAE), a disease resembling multiple sclerosis (MS) that can be induced in susceptible animals. Batches of this copolymer of average molecular weight 23,000 Daltons (Da), designated "Copolymer" 1 or "Cop" 1, were shown to be highly effective in protecting and suppressing EAE in several animal species (Teitelbaum et al. 1971, *Eur. J. Immunol.* 1(4), 242-248; Teitelbaum et al. 1974, *Clin. Immunol. Immunopathol.* 3(2), 256-262; Teitelbaum et al. 1974, *Israel J. Med. Sci.* 13:1038).

Later, Copolymer 1 was found to significantly reduce the number of relapses in patients with the exacerbating-remitting form of multiple sclerosis (Bornstein et al. 1990, *Handbook of Multiple Sclerosis*, ed. Cook S. D. Marcel Dekker, Inc., p. 469; Sela et al. 1990, *Bull. Inst. Pasteur* (Paris) 88, 303-314; Johnson et al. 1994, *MS. 11th Annual Meeting A.N.A.*). Copolymer 1, in the form of the acetate salts of synthetic polypeptides containing L-Glu, L-Ala, L-Tyr and L-Lys with an average molar fraction of 0.141, 0.427, 0.095 and 0.338, respectively, is the active ingredient of COPAXONE®, a medicament for the treatment of multiple sclerosis. COPAXONE® is the registered trade name for glatiramer acetate. Chemically, glatiramer acetate or Copolymer 1 is designated L-Glu polymer with L-Ala, L-Lys, and L-Tyr, acetate salt, and its structural formula is:

(Glu,Ala,Lys,Tyr)$_x$·xCH$_3$COOH
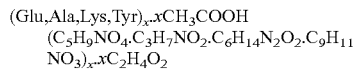
NO$_3$)$_x$·xC$_2$H$_4$O$_2$

The effect of Copolymer 1 in the treatment of multiple sclerosis is in the achievement of suppression or deactivation of autoimmune T cell reactivity to myelin antigens in multiple sclerosis patients. For this purpose, Copolymer 1 is administered without adjuvants by daily subcutaneous injection.

Copolymer 1 was originally designed to mimic myelin basic protein (MBP) and to induce EAE, but was found to be non-encephalitogenic and to even suppress EAE induced by MBP (Teitelbaum et al. 1971, *Eur. J. Immunol.* 1(4), 242-248), proteolipid protein (PLP) (Teitelbaum et al. 1996, *J. Neuroimmunol.* 64, 209-217), or oligodendrocyte glycoprotein (MOG) (Ben-Nun et al. 1996, *J. Neurol.* 243(4Sup1), S14-22). The precise mechanisms by which Copolymer 1 prevents the development of EAE and ameliorates multiple sclerosis (MS) are not yet known. Nevertheless, some important immunological properties of this copolymer have emerged. Studies have demonstrated partial cross-reactivity of Copolymer 1 with MBP at both the T cell (Webb et al. 1973, *Immunol. Commun.* 2(2), 185-192) and the antibody (Teitelbaum et al. 1988, *Proc. Natl. Acad. Sci. USA* 85(24), 9724-9728) level. Copolymer 1 can serve as an antagonist of the T-cell antigen receptor for the MBP immunodominant epitope (Aharoni et al. 1988, *J. Neuroimmunol.* 91(1-2), 135-146). It can also bind to various MHC class II molecules and prevent them from binding to T cells with specific antigen-recognition properties (Fridkis-Hareli et al. 1999, *Int. Immunol.* 11(5), 635-641).

Currently COPAXONE® is approved for reduction of the frequency of relapses in patients with Relapsing-Remitting Multiple Sclerosis (RRMS). The composition, its manner of manufacture and methods of treatment using same are described in U.S. Pat. Nos. 5,981,589; 6,054,430; 6,342,476; 6,362,161; 6,620,847; 6,939,539. Further extensive uses of Copolymer 1 and related peptides and polypeptides as well as T cells treated therewith for neuroprotective therapy is disclosed in numerous publications and patents including WO 01/93893, U.S. Pat. Nos. 6,835,711 and 6,844,314, among others.

Recently it was found that in animal models, Copolymer 1 provides beneficial effects in several additional disorders. Thus, Copolymer 1 suppresses the immune rejection manifested in graft versus host disease (GVHD) in case of bone marrow transplantation (U.S. Pat. No. 5,858,964), as well as in graft rejection in case of solid organ transplantation (WO 00/27417).

WO 01/52878 and WO 01/93893 disclose that Copolymer 1 and related peptides and polypeptides as well as T cells activated by these peptides and polypeptides protect central nervous system (CNS) cells from glutamate toxicity and prevent or inhibit neuronal degeneration or promote nerve regeneration in the CNS and peripheral nervous system (PNS). Copolymer 1 has also been proposed as a treatment for neurodegenerative diseases such as optic neuropathies and glaucoma. WO 08/075,365 discloses the use of random or ordered copolymers including Copolymer 1 for treating, preventing, delaying or diminishing age-related deterioration of retinal function.

Copolymer 1 and related copolymers and peptides have been disclosed for treating autoimmune diseases other than multiple sclerosis in WO 00/05250. WO 00/27417 discloses compositions and methods for treating and preventing host-versus-graft immune responses and graft-versus-host diseases comprising as an active ingredient Copolymer 1 and Copolymer 1-related random heteropolymers.

There is an unmet medical need for new compositions for the treatment of autoimmune diseases and, in particular, multiple sclerosis, with desired pharmacological profile and few side effects.

SUMMARY OF THE INVENTION

The present invention provides a synthetic polypeptide which is a random pentapolymer or a salt thereof, comprising alanine, glutamic acid, lysine, tyrosine and phenylalanine, useful for the treatment of autoimmune diseases and, in particular multiple sclerosis (MS). The pentapolymer is a copolymer of alanine, glutamic acid, lysine, tyrosine and phenylalanine, which are randomly polymerized into a polypeptide, thereby forming a random copolymer, or a salt thereof.

The present invention is based in part on the unexpected finding that the novel pentapolymer shows unexpected oral bioavailability, an advantageous release profile when formulated into a depot drug delivery system and advantageous synergistic activity in autoimmune diseases when combined with an additional therapeutic agent.

According to a first aspect, the present invention provides a pentapolymer or a salt thereof, which is a linear random copolymer of alanine, glutamic acid, lysine, tyrosine and phenylalanine.

According to another aspect, the present invention provides a pentapolymer or a salt thereof, which is a linear copolymer of alanine, glutamic acid, lysine, tyrosine and phenylalanine, randomly polymerized into a polypeptide.

According to another aspect, the present invention provides a pentapolymer or a salt thereof, the pentapolymer consisting essentially of alanine, glutamic acid, lysine, tyrosine and phenylalanine randomly polymerized into a polypeptide.

In another embodiment, the present invention provides a pentapolymer or a salt thereof, the pentapolymer consisting of alanine, glutamic acid, lysine, tyrosine and phenylalanine randomly polymerized into a polypeptide.

In some embodiments, the molar ratio of the amino acids in the pentapolymer is the following: from about 2.0 to about 3.2 alanine; from about 1.4 to about 2.0 glutamic acid; from about 4.4 to about 4.6 lysine; from about 0.9 to about 1.1 tyrosine and from about 0.8 to about 1.2 phenylalanine.

In one embodiment, the pentapolymer comprises alanine, glutamic acid, lysine, tyrosine and phenylalanine wherein the molar ratio of alanine to glutamic acid to lysine to tyrosine to phenylalanine is about 2.5:1.9:4.5:1.0:0.9, respectively.

In various embodiments of the present invention, the pentapolymer comprises from about 15 to about 120 amino acids, for example from about 40 to about 80 amino acids in length, or from about 60 to about 100 amino acids in length. Each possibility represents a separate embodiment of the present invention.

In certain embodiments, the average molecular weight of the pentapolymer of the invention may be in the range of about 2,000 to about 20,000 Da. In other embodiments, the average molecular weight of the pentapolymer of the invention is about 5,000-15,000 Da. In other embodiments, the average molecular weight of the pentapolymer of the invention is about 5,000-10,000 Da.

The pentapolymer of the present invention may be composed of L- or D-amino acids or mixtures thereof. As is known by those of skill in the art, L-amino acids occur in most natural proteins. However, D-amino acids are commercially available and can be substituted for some or all of the amino acids used to make the pentapolymer of the present invention. The present invention contemplates a pentapolymer containing both D- and L-amino acids, as well as pentapolymers having either L- or D-amino acids.

The present invention further provides a pharmaceutical composition comprising a therapeutically effective amount of the pentapolymer of the invention and a pharmaceutically acceptable carrier.

In additional embodiments, the pharmaceutical composition can be administered by any convenient route including, but not limited to, the parenteral route by subcutaneous (SC), intravenous (IV), intramuscular (IM), intradermal (ID), and intraperitoneal (IP) injection. Each possibility represents a separate embodiment of the present invention.

In one embodiment, the pharmaceutical composition of the present invention can be formulated for oral administration.

In some embodiments, the present invention provides a long acting pharmaceutical composition comprising a therapeutically effective amount of the pentapolymer of the present invention in a depot form suitable for administration at a medically acceptable location in a subject in need thereof. In accordance with these embodiments, the pharmaceutical composition further comprises a pharmaceutically acceptable biodegradable or non-biodegradable carrier selected from PLGA, PLA, PGA, polycaprolactone, polyhydroxybutyrate, polyorthoesters, polyalkane anhydrides, gelatin, collagen, oxidized cellulose, and polyphosphazene, or any combination thereof. Each possibility represents a separate embodiment of the present invention.

The pentapolymer of the present invention or a pharmaceutical composition comprising same is useful for treating an autoimmune disease. In particular embodiments, the disease treated is an autoimmune disease of the central nervous system. In accordance with these embodiments, the present invention provides a method of treating an autoimmune disease comprising administering to a subject in need thereof an effective amount of a pharmaceutical composition comprising a pentapolymer of the present invention as an active ingredient. In another embodiment, the present invention relates to the use of a pentatolymer according to the present invention for the treatment of an autoimmune disease. In another embodiment, the present invention relates to the use of a pentatolymer according to the present invention for the manufacture of a medicament for the treatment of an autoimmune disease. In some embodiments, the pentapolymer is administered in a long acting pharmaceutical formulation as described herein.

Autoimmune diseases within the scope of the present invention include, but are not limited to, multiple sclerosis (including Relapsing-Remitting multiple sclerosis (RRMS)), autoimmune hemolytic anemia, autoimmune oophoritis, autoimmune thyroiditis, autoimmune uveoretinitis, Crohn's disease, chronic immune thrombocytopenic purpura, colitis, contact sensitivity disease, diabetes mellitus, Graves disease, Guillain-Barre's syndrome, Hashimoto's disease, idiopathic myxedema, myasthenia gravis, psoriasis, pemphigus vulgaris, rheumatoid arthritis, and systemic lupus erythematosus. Each possibility represents a separate embodiment of the present invention. In particular embodiments, the pentapolymer of the present invention is useful in treating multiple sclerosis (MS). In some currently preferred embodiments, the pentapolymer of the present invention is useful in treating Relapsing-Remitting multiple sclerosis (RRMS). According to various embodiments of the present invention, the pentapolymer may be used in combination therapy with at least one other active agent, as described herein.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention relates to a pentapolymer or a salt thereof, which is a linear random copolymer of alanine, glutamic acid, lysine, tyrosine and phenylalanine. The present invention further relates to pharmaceutical compositions comprising the pentapolymer and use thereof in treating autoimmune diseases and in particular multiple sclerosis (MS), for example Relapsing-Remitting MS (RRMS).

As used herein, the term "pentapolymer" refers to a copolymer or polypeptide which is composed of the five amino acids alanine, glutamic acid, lysine, tyrosine and phenylalanine, in various ratios as described herein.

As used herein, the terms "random copolymer" or "randomly polymerized into a polypeptide" refers to a copolymer or polypeptide having a random amino acid sequence. The copolymers of the present invention are linear copolymers.

In any of the disclosed embodiments, the pentapolymers of the present invention may in the form of a pharmaceutically acceptable salt, which may be an acid addition salt wherein the acid is an organic or inorganic acid. In one preferred embodiment, the salt is an acetate salt. In other embodiments, the acid addition salts include, but are not limited to, salts derived from hydrochloric, hydrofluoric, trifluoroacetic, sulfuric, phosphoric, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the present invention.

According to the principles of the present invention, the pentapolymer disclosed herein comprises from about 15 to about 120 amino acids. In one embodiment, the pentapolymer comprises from about 40 to about 80 amino acids in length. In another embodiment, the pentapolymer comprises from about 60 to about 100 amino acids in length.

The pentapolymer is a linear random copolymer of alanine, glutamic acid, lysine, tyrosine and phenylalanine. In another embodiment, the copolymer is a linear random copolymer consisting essentially of alanine, glutamic acid, lysine, tyrosine and phenylalanine. In another embodiment, the copolymer is a linear random copolymer consisting of alanine, glutamic acid, lysine, tyrosine and phenylalanine.

The average molecular weight of the pentapolymer of the invention is about 2,000-20,000 Da. In some embodiments, the average molecular weight of the pentapolymer is about 5,000-15,000 Da. In other embodiments, the average molecular weight of the pentapolymer is about 5,000-10,000 Da. In other embodiments, the average molecular weight of the pentapolymer is about 7,500-15,000 Da. In other embodiments, the average molecular weight of the pentapolymer is about 7,500-10,000 Da.

The molecular weight of the pentapolymer can be adjusted during polypeptide synthesis or after the pentapolymer has been prepared. To adjust the molecular weight during polypeptide synthesis, the synthetic conditions or the amounts of amino acids are adjusted so that synthesis stops when the polypeptide reaches the approximate desired length. After synthesis, polypeptides with the desired molecular weight can be obtained by any available size selection procedure, such as chromatography of the polypeptides on a molecular weight sizing column or gel, and collection of the molecular weight ranges desired. The pentapolymer of the present invention can also be partially hydrolyzed to remove high molecular weight species, for example, by acid or enzymatic hydrolysis, and then purified to remove the acid or enzymes. Alternatively the desired size can be reached by adjusting the amount of the initiator introduced.

The pentapolymer of the present invention may be prepared in accordance with methods similar to those described in the literature for the preparation of Copolymer 1 and related peptides, for example U.S. Pat. No. 3,849,550, U.S. Pat. No. 5,800,808, U.S. Pat. No. 5,981,589, U.S. Pat. No. 6,054,430, U.S. Pat. No. 6,342,476, U.S. Pat. No. 6,362,161, U.S. Pat. No. 6,620,847, U.S. Pat. No. 6,939,539 and EP 1799703, the contents of each of which is incorporated by reference herein. For example, the pentapolymer of the desired molecular weight may be prepared by polymerizing the N-carboxyanhydrides of tyrosine, alanine, γ-benzyl-glutamate, N-6-trifluoroacetyl lysine, and phenylalanine at ambient temperature in a solvent and an initiator so as to obtain a protected polypeptide. Suitable initiators are nucleophiles such as amines (preferably secondary amines such as diethylamine), alcohols, water etc. The protected polypeptide is then reacted with hydrobromic acid which removes the benzyl protecting group from the 5-carboxylate of the glutamate residue and cleaves the polymer to smaller polypeptides to form a trifluoroacetyl-polypeptide having the desired molecular weight profile. The time needed for obtaining a polypeptide of a desired molecular weight range will typically depend on the temperature of the reaction and the size of the protected polypeptide. Thus, in some embodiments, the reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by the test reaction. The trifluoroacetyl-polypeptide with the desired molecular weight profile is then further treated with an aqueous piperidine solution to form a deprotected polypeptide having the desired molecular weight.

The nature of the solvent used for the reaction is not particularly limiting. Some examples include, but are not limited to aromatic hydrocarbons such as benzene, toluene, and xylene; ethers such as diethyl ether, MTBE, diisopropyl ether, tetrahydrofuran (THF), 1,4-dioxane, 1,2-dimethoxyethane, and 1,2-diethoxyethane; halogenated hydrocarbons such as dichloromethane, 1,2-dichloroethane, and chloroform, N-dimethylformamide (DMF), N-methylpyrrolidone (NMP), dimethyl sulfoxide (DMSO), and any mixtures thereof. Each possibility represents a separate embodiment of the present invention. Dioxane is a currently preferred solvent. In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

The pentapolymer of the present invention may be composed of L- or D-amino acids or a mixture of L- and D-amino acids. As is known by those of skill in the art, L-amino acids occur in most natural proteins. However, D-amino acids are commercially available and can be substituted for some or all of the amino acids used to make the pentapolymers of the present invention. The present invention contemplates pentapolymers containing both D- and L-amino acids, as well as pentapolymers consisting essentially of either L- or D-amino acids.

The pentapolymer of the present invention comprises alanine, glutamic acid, lysine, tyrosine and phenylalanine in the molar ratios of: from about 2.0 to about 3.2 alanine; from about 1.4 to about 2.0 glutamic acid; from about 4.4 to about 4.6 lysine; from about 0.9 to about 1.1 tyrosine and from about 0.8 to about 1.2 phenylalanine. In one embodiment, the pentapolymer comprises alanine, glutamic acid, lysine, tyrosine and phenylalanine in the molar ratios of alanine about 2.5 to glutamic acid about 1.9 to lysine about 4.5 to tyrosine about 1.0 to phenylalanine about 0.9.

In another embodiment, the pentapolymer of the present invention comprises alanine, glutamic acid, lysine, tyrosine and phenylalanine in the molar ratios of: from about 3.0 to about 4.2 alanine; from about 1.4 to about 1.6 glutamic acid; from about 3.4 to about 3.6 lysine; from about 0.9 to about 1.1 tyrosine and from about 1.4 to about 1.6 phenylalanine. In one embodiment, the pentapolymer comprises alanine, glutamic acid, lysine, tyrosine and phenylalanine in the molar ratios of alanine about 3.5 to glutamic acid about 1.5 to lysine about 3.5 to tyrosine about 1.0 to phenylalanine about 1.5.

The present invention further provides a pharmaceutical composition comprising the pentapolymer disclosed herein and a pharmaceutically acceptable carrier. As used herein, "pharmaceutically acceptable carrier" includes any or all solvents, dispersion media, coatings, antibacterial and antifungal agents, isotonic and absorption delaying agents, sweeteners and the like. The pharmaceutically acceptable carriers may be prepared from a wide range of materials including, but not limited to diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents with pharmaceutically active substances are well known in the art. Except insofar as any conventional media or agent is incompatible with the active ingredient, its use in the therapeutic compositions is contemplated.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the pentapolymer of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants, for example DMSO or polyethylene glycol are generally known in the art.

For oral administration, the pentapolymer can be formulated with pharmaceutically acceptable carriers well known in the art as tablets, pills, dragees, capsules, liquids, gels, syrups, slurries, suspensions, and the like, for oral ingestion by a patient. The preparation of the pharmaceutical compositions can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredient in admixture with filler such as lactose, binders such as starches, lubricants such as talc or magnesium stearate and, optionally, stabilizers.

In soft capsules, the pentapolymer may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Pharmaceutical compositions for parenteral administration include aqueous solutions of the pentapolymer in water-soluble form as well as suspensions of the pentapolymer. The term "parenteral" as used herein refers to routes selected from subcutaneous (SC), intravenous (IV), intramuscular (IM), intradermal (ID), intraperitoneal (IP) and the like. Suitable lipophilic solvents or vehicles include fatty oils such as sesame oil, or synthetic fatty acid esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

Other routes of administration include nasal administration and oral inhalation to the mucosal linings of the trachea and bronchial passages.

According to various embodiments of the present invention, the therapeutically effective amount of the pentapolymer ranges from about 1 mg to about 500 mg/day. Alternatively, such therapeutically effective amounts of the pentapolymer are from about 20 mg to about 100 mg/day. Alternatively, such therapeutically effective amounts of the pentapolymer are from about 1 mg to about 100 mg/day. Alternatively, such therapeutically effective amounts of the pentapolymer are from about 100 mg to about 200 mg/day. In some embodiments, the present invention provides a long acting parenteral pharmaceutical composition in the form of a depot comprising a therapeutically effective amount of the pentapolymer disclosed herein. The term "therapeutically effective amount" as used herein is intended to qualify the amount of pentapolymer that will achieve the goal of alleviation of the symptoms of the autoimmune disease (e.g. 20-750 mg). However, it is understood that the amount of the pentapolymer administered will be determined by a physician, according to various parameters including the chosen route of administration, the age, weight, and the severity of the patient's symptoms. The term "long acting" as used herein refers to a composition which provides prolonged, sustained or extended release of the pentapolymer to the general systemic circulation of a subject or to local sites of action in a subject. This term may further refer to a composition which provides prolonged, sustained or extended duration of action (pharmacokinetics) of the pentapolymer in a subject. In particular, the long acting pharmaceutical compositions of the present invention provide a dosing regimen which ranges from once weekly to once every 6 months. According to currently more preferable embodiments, the dosing regimen ranges from once a week, twice monthly (approximately once in every 2 weeks) to once monthly. Depending on the duration of action required, each depot or implantable device of the present invention will typically contain between about 20 and 750 mg of the active ingredient, designed to be released over a period ranging from several weeks to several months.

In some embodiments, the depot formulations of the present invention include, but not limited to, biodegradable injectable depot systems such as, PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(ϵ-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly (p-{carboxyphenoxy}methane), CPM; poly(p-{carboxyphenoxy} propane), CPP; poly(p-{carboxyphenoxy}hexane), CPH; polyamines, polyurethanes, polyesteramides, polyorthoesters {CHDM: cis/trans-cyclohexyl dimethanol}, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) tri-block copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof. Each possibility represents a separate embodiment of the present invention.

In some embodiments, the compositions of the present invention comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. Each possibility represents a separate embodiment of the invention.

Currently preferred biodegradable polymer is a lactic acid-based polymer, more preferably polylactide, or poly (D, L-lactide-co-glycolide) i.e. PLGA. Preferably, the biodegradable polymer is present in an amount between about 10% to about 98% w/w of the composition. The lactic acid-based polymer has a monomer ratio of lactic acid to glycolic acid in the range of 100:0 to about 0:100, preferably 100:0 to about 10:90 and has an average molecular weight of from about 1,000 to about 200,000 Da. However, it is understood that the amount of biodegradable polymer is determined by parameters such as the duration of use and the like.

The long acting compositions of the present invention may further comprise one or more pharmaceutically acceptable excipient(s) selected from, but not limited to, co-surfactants, solvents/co-solvents, water immiscible solvents, water, water miscible solvents, oily components, hydrophilic solvents, emulsifiers, preservatives, antioxidants, anti-foaming agents, stabilizers, buffering agents, pH adjusting agents, channel forming agents, osmotic adjustment agents, or any other excipient known in the art. Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment of the invention. Suitable solvents/co-solvents include, but not limited to, alcohols, triacetin, dimethyl isosorbide, glycofurol, propylene carbonate, water, dimethylacetamide, and the like or mixtures thereof. Each possibility represents a separate embodiment of the invention. Suitable anti-foaming agents include, but are not limited to, silicon emulsions or sorbitan sesquioleate. Suitable stabilizers to prevent or reduce the deterioration of the components in the compositions of the present invention include, but are not limited to, antioxidants such as glycine, α-tocopherol or ascorbate, butylated hydroxyanisole (BHA), butylated hydroxytoluene (BHT), and the like or mixtures thereof. Each possibility represents a separate embodiment of the invention. Suitable tonicity modifiers include, but are not limited to, mannitol, sodium chloride, and glucose. Each possibility represents a separate embodiment of the invention. Suitable buffering agents include, but are not limited to, acetates, phosphates, and citrates with suitable cations. Each possibility represents a separate embodiment of the invention.

The long acting compositions of the present invention can be prepared by any manner known in the art. Currently preferred is the incorporation of the pentapolymer into a colloidal delivery system, e.g., biodegradable microparticles, thus allowing release retardation by diffusion through polymeric walls of the particle and by polymer degradation in water media or biological fluids in the body. The compositions of the present invention can be prepared in the form of injectable microparticles by a process known as the "double emulsification". Briefly, the concentrated solution of the water-soluble pentapolymer is dispersed in a solution of the biodegradable or non-biodegradable polymer in water-immiscible volatile organic solvent (e.g. methylene chloride, chloroform and the like). The thus obtained "water-in-oil" (w/o) emulsion is then dispersed in a continuous external water phase containing surfactant (e.g. polyvinyl alcohol—PVA, polysorbates, polyethylene oxide-polypropylene oxide block copolymers, cellulose esters and the like) to form "water-in oil-in water (w/o/w) double emulsion" droplets. After evaporation of the organic solvent, the microparticles solidify and are collected by filtration or centrifugation. The collected microparticles (MPs) are washed with purified water to eliminate most of the surfactant and non-bonded peptide and centrifugated again. The washed MPs are collected and lyophilized without additives or with the addition of cryoprotectant (e.g. mannitol) to facilitate their subsequent reconstitution.

The depot systems of the present invention encompass any forms known to a person of skill in the art. Suitable forms include, but are not limited to, biodegradable or non biodegradable microspheres, implantable rods, implantable capsules, and implantable rings. Each possibility represents a separate embodiment of the invention. Further contemplated are prolonged release gel depot and erodible matrices. Each possibility represents a separate embodiment of the invention. Suitable implantable systems are described for example in US 2008/0063687, the content of which is hereby incorporated in its entirety. Implantable rods can be prepared as is known in the art using suitable micro-extruders such as those described for example in http://www.randcastle.com/prodinfo.html.

According to the principles of the present invention, the long acting pharmaceutical compositions of the present invention provide unexpected advantageous release profile of the active ingredient thus providing superior therapeutic efficacy.

Therapeutic Uses

The pentapolymer of the present invention as well as the pharmaceutical compositions comprising same are useful for the treatment of autoimmune diseases. Autoimmune diseases within the scope of the present invention include, but are not limited to, multiple sclerosis, autoimmune hemolytic anemia, autoimmune oophoritis, autoimmune thyroiditis, autoimmune uveoretinitis, Crohn's disease, chronic immune thrombocytopenic purpura, colitis, contact sensitivity disease, diabetes mellitus, Graves disease, Guillain-Barre's syndrome, Hashimoto's disease, idiopathic myxedema, myasthenia gravis, psoriasis, pemphigus vulgaris, rheumatoid arthritis, and systemic lupus erythematosus. Each possibility represents a separate embodiment of the present invention.

Currently preferred is the treatment of multiple sclerosis (MS), including Relapsing-Remitting multiple sclerosis (RRMS). The term "multiple sclerosis" as used herein refers to an autoimmune disease of the central nervous system which is accompanied by one or more of the following symptoms: reduced or loss of vision, stumbling and uneven gait, slurred speech, as well as urinary frequency and incontinence. Additional symptoms include mood changes and depression, muscle spasms and severe paralysis. The term "treating" as used herein refers to suppression or alleviation of any of the described symptoms.

In some embodiments, the pentapolymer of the present invention is used to reduce the frequency of relapses in patients with Relapsing-Remitting Multiple Sclerosis.

Encompassed by the present invention is a combination therapy of the pentapolymer disclosed herein with at least one other active agent. Active agents within the scope of the present invention include, but are not limited to interferons, e.g. pegylated or non-pegylated α-interferons, or β-interferons, e.g. interferon β-1a or interferon β-1b, or τ-interferons; immunosuppressants optionally with antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH; adenosine deaminase inhibitors, e.g. cladribine; IV immunoglobulin G (e.g. as disclosed in Neurology, 1998, May 50(5):1273-81) monoclonal antibodies to various T-cell surface markers, e.g. natalizumab (ANTEGREN®) or alemtuzumab; TH2 promoting cytokines, e.g. IL-4, IL-10, or compounds which inhibit expression of TH1 promoting cytokines, e.g. phosphodiesterase inhibitors, e.g. pentoxifylline; antispasticity agents including baclofen, diazepam, piracetam, dantrolene, lamotrigine, rifluzole, tizanidine, clonidine, beta blockers, cyproheptadine, orphenadrine or cannabinoids; AMPA glutamate receptor antagonists, e.g. 2,3-dihydroxy-6-nitro-7-sulfamoylbenzo(f)quinoxaline, [1,2,3,4,-tetrahydro-7-morpholin-yl-2,3-dioxo-6-(trifluoromethyl)quinoxalin-1-yl]methylphosphonate, 1-(4-aminophenyl)-4-methyl-7,8-methylene-dioxy-5H-2,3-benzodiazepine, or (−)1-(4-aminophenyl)-4-methyl-7,8-methylenedioxy-4,5-dihydro-3-methylcarbamoyl-2,3-benzodiazepine; inhibitors of VCAM-1 expression or antagonists of its ligand, e.g. antagonists of the α4β1 integrin VLA-4 and/or α-4-β-7 integrins; anti-macrophage migration inhibitory factor (Anti-MIF); xii) Cathepsin S inhibitors; xiii) mTor inhibitors. Each possibility represents a separate embodiment of the invention. Currently preferred one other active agent is FTY720 (2-amino-2-[2-(4-octylphenyl)ethyl]propane-1,3-diol; fingolimod) or its pharmaceutically acceptable salts belonging to the class of immunosuppressants.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Example 1

Preparation of the Pentapolymer

The pentapolymer was prepared following the method described in U.S. Pat. No. 5,800,808 (Examples 3 and 4; the content of which is hereby incorporated in its entirety), using the following molar ratios of the N-carboxyanhydrides (NCA) of protected tyrosine (1 mol), alanine (2.5 mol), γ-benzyl-glutamate (1.9 mol), trifluoroacetyl-lysine (4.5 mol) and phenylalanine (1 mol).
Analytical Characterization Data of the Product:
pH=7.17 (20 mg/mL);
Average MW=6,591;
Purity=85%;
MW distribution=88.1%>2,500 Da; 90.7%<21,000 Da.

Example 2

Preparation of a Long Acting Formulation of the Pentapolymer

PLGA-based injectable depot particles were prepared by solvent extraction/evaporation method (single emulsion). A solution of 50:50, dichloromethane/ethanol containing 250 mg PLGA and 200 mg of the pentapolymer of the present invention was slowly poured into an aqueous solution (200 ml) containing 2% PVA and emulsified using a mechanical stirrer (300 rpm) at 25° C. The organic solvent was evaporated under stirring (100 rpm) for 2 h. The thus formed microparticles were collected by centrifugation and washed with distilled water to remove excessive emulsifier. The final suspension was then freeze-dried to obtain a fine powder.

Example 3

Experimental Autoimmune Encephalomyelitis (EAE) Model

Experimental autoimmune encephalomyelitis (EAE) is an inflammatory autoimmune demyelinating disease which can be induced in laboratory animals by injection of myelin basic protein. Such disease has become the standard laboratory model for studying clinical and experimental autoimmune diseases. In fact, numerous articles (e.g., Abramsky et. al., 1982, J Neuroimmunol 2, 1 and Bolton et al., 1982, J Neurol Sci. 56, 147) note that the similarities of chronic relapsing EAE in animals to multiple sclerosis in humans especially implicates the value of EAE for the study of autoimmune demyelinating diseases such as multiple sclerosis. As such, the EAE test model is employed to establish the activity of the pentapolymer of the present invention against multiple sclerosis. Such testing is conducted according to the following procedure.

Female Lewis rats are injected in their footpads with 12.5 µg of myelin basic protein (MBP) (prepared form guinea-pig spinal cord) in Complete Freunds adjuvant. The pentapolymer of the present invention is given by injection every day at various dosages to the test animals. Gold standard regimen of glatiramer acetate (e.g. PNAS, 2005, vol. 102, no. 52, 19045-19050) is given to certain other test animals as control. The animals are then weighed and scored daily for symptoms of EAE according to a scale of 0 to 3 (0=no change; 1=flaccid tail; 2=hind limb disability and 3=hind quarter paralysis/moribund). Animals are then sacrificed if a score of 3 is reached.

Example 4

In Vivo Studies Using the EAE Model

To determine the effect of the pentapolymer of the present invention on the murine model of MS, experimental autoimmune encephalomyelitis (EAE) is performed. EAE is induced by injection of emulsion of MOG (Myelin Oligodendrocyte Glycoprotein) subcutaneously on the shaved back of the mouse (C57BL/6 mice are used) at three sites, followed by an intraperitoneal injection of *Bordetella pertussis* toxin in Phosphate Buffered Saline on Day 0 and 48 hours post MOG immunization. EAE is assessed by clinical scoring of the mice once daily from Day 0 to indicated days post immunization, as described below. The disease incidence and group mean score is determined and the treatment groups are compared to non-treatment control.

The following test articles are used:
(a) A pentapolymer formulation according to the present invention (PP);
(b) A conventional glatiramer acetate injectable formulation (GA); and
(c) A depot formulation containing glatiramer acetate (GA-depot) as described in WO 2011/080733, the content of which is hereby incorporated by reference in its entirety.

Test Article Preparation:
PP and GA formulations are dissolved in water-for-injection (WFI). GA depot is suspended in WFI, vortexed and if necessary sonicated up to 10 minutes without heating, until a homogenous white suspension is obtained, capable of being withdrawn and injected via an adequate needle.

Vehicle Information:
Vehicle 1: saline, 0.9% NaCl in sterile water
Vehicle 2: water for injection (WFI)
Reagents:
MOG 35-55: (GL BiochemCo. Ltd; Shanghai, P. R. China). MOG 35-55 is dissolved in saline to a concentration of 2 mg/mL.
Complete Freund's adjuvant (CFA) (Cat: F5881; Sigma-Aldrich; St. Louis, Mo., USA). Heat-killed *Mycobacterium tuberculosis* strain H37RA (Cat: 231141; Difco; Detroit, Mich., USA) is added to complete Freund's adjuvant to a final concentration of 4 mg/mL.
*Bordetella pertussis* toxin (PTX): (Cat: P7208; Sigma-Aldrich; St. Louis, Mo., USA).

Using a high-speed homogenizer, the above MOG solution is emulsified with equal volume of the modified CFA on ice for 30,000 rpm for 1.5 hour.

Animals:
C57BL/6 mice, female, 7-9 weeks, 17-20 g.
Adaptation: not less than 7 days.
Room: Specific Pathogen Free (SPF) room
Room temperature: 20-26° C.
Room relative humidity: 40-70%
Light cycle: fluorescent light for 12-hour light (08:00-20:00) and 12-hour dark.
Animal hosting: 3-4 mice/cage by treatment group
Food: free access to food (irradiated, Shanghai SLAC Laboratory Animal Co. Ltd., China).
Water: free access to water (municipal tap water filtered by Mol Ultrapure Water System).

Allocation to Treatment Groups:
Animals are assigned to treatment groups by randomization in Biobook software to achieve similar group mean weight, which provides for control of bias.

TABLE 1

Group and dosing regimen

| Group | Test Article | N | Route | Conc. mg/mL | Dosage mL/mice | mg/mice | Regimen | Dose on (days) |
|---|---|---|---|---|---|---|---|---|
| 1 | PP[b] | 10 | s.c. | 10 | 0.2 | 2 | q.d. | D0-9 |
| 2 | GA[b] | 10 | i.m. | 25 | 0.2 | 5 | q.d. | D0, 1, 14, 15, 28, 29 |
| 3 | GA[b] | 10 | i.m. | 25 | 0.2 | 5 | q.d. | D0, 14, 28 |
| 4 | GA[b] | 10 | i.m. | 25 | 0.2 | 5 | q.d. | D0, 7, 14, 21, 28 |
| 5 | GA-depot[b] | 10 | i.m. | 312 | 0.2 | 62.5* | q.d. | D0, 1, 14, 15, 28, 29 |
| 6 | GA-depot[b] | 10 | i.m. | 312 | 0.2 | 62.5* | q.d. | D0, 14, 28 |
| 7 | GA-depot[b] | 10 | i.m. | 312 | 0.2 | 62.5* | q.d. | D0, 7, 14, 21, 28 |
| 8 | GA[b] | 10 | s.c. | 10 | 0.2 | 2 | q.d. | D0-9 |
| 9 | Veh[a] | 10 | s.c. | N/A | 0.2 | N/A | q.d. | D0-9 |

[a]Vehicle is saline
[b]Vehicle is WFI
*GA content is 80 mg/g of "GA-depot" formulated product, i.e. 5 mg/mice/day of GA.

After anesthetization by isoflurane (2-3%, inhalation), EAE is induced by injecting 100 µL emulsion subcutaneously into the shaved backs of the mice. *Bordetella pertussis* toxin (200 ng in 200 µL of PBS) is administered i.p. on the day of immunization (Day 0) and 48 hours thereafter.

Mice are treated with the pentapolymer of the present invention which is administered by injection once daily at various dosages. Control groups are treated either with placebo or with Gold standard regimen of glatiramer acetate (GA) (e.g. PNAS, 2005, vol. 102, no. 52, 19045-19050), or with a depot formulation containing glatiramer acetate (GA depot).

Test article or vehicle is administered to each group according to the treatment regimes and dosing described in Table 1.

Group 1: PP, 2 mg/mice s.c. for 10 days (days 0 to day 9). Follow-up for 30 days.

Group 2: GA, i.m. administration, 5 mg/mice on day 0 and day 1, day 14 and day 15, day 28, day 29. Follow-up for 45 days.

Group 3: GA, i.m. administration, 5 mg/mice on day 0, day 14, day 28. Follow-up for 45 days Group 4: GA, i.m. administration, 5 mg/mice on day 0, day 7, day 14, day 21, day 28. Follow-up for 45 days.

Group 5: GA (depot) i.m. administration. Quantities are on the basis of active material. The content of the active GA is 80 mg/g of formulation. 5 mg/mice on day 0 and day 1, day 14 and day 15, day 28, day 29. Follow-up for 45 days.

Group 6: GA (depot) i.m. administration, 5 mg/mice on day 0, day 14, day 28. Follow-up for 45 days.

Group 7: GA (depot) i.m. administration, 5 mg/mice on day 0, day 7, day 14, day 21, day 28. Follow-up for 45 days.

Group 8: GA, 2 mg/mice s.c. for 10 days (days 0 to day 9). Follow-up for 30 days.

Group 9: control group of vehicle (saline).

Body weights of all mice are recorded daily starting from Day 0 to Day 30 for Group 1, Group 8, and Group 9. Other Groups are recorded from Day 0 to Day 45. The mice are examined daily for clinical signs of EAE utilizing the following scoring system: 0=normal mouse; 1=limp tail or hind limb weakness; 2=limp tail and hind limb weakness; 3=partial hind limb paralysis; 4=complete hind limb paralysis; and 5=moribund state. The incidence, mortality and group mean score is determined and the treatment groups are compared to non-treatment control.

Mean body weight among the groups is compared by ANOVA followed by Dunnett's post-Hoc test. Comparisons of the mean clinical score between two groups are made by Mann-Whitney test. Incidences of disease between two groups are compared among the groups by Peason Chi-square test. $P<0.05$ are considered statistically significant.

All references cited herein are hereby expressly incorporated by reference in their entirety. While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A pentapolymer or a salt thereof, which is a linear random copolymer of alanine, glutamic acid, lysine, tyrosine and phenylalanine, wherein the molar ratio of alanine to glutamic acid to lysine to tyrosine to phenylalanine is about 2.5:1.9:4.5:1.0:0.9, respectively.

2. The pentapolymer according to claim 1, containing from about 15 to about 120 amino acids.

3. The pentapolymer according to claim 2, having an average molecular weight of about 2,000 to about 20,000 Da.

4. The pentapolymer according to claim 3, having an average molecular weight of about 5,000 to about 15,000 Da.

5. The pentapolymer according to claim 1, comprising L amino acids, D-amino acids or a mixture of L- and D-amino acids.

6. A pharmaceutical composition comprising a therapeutically effective amount of the pentapolymer according to claim 1 and a pharmaceutically acceptable carrier.

7. The pharmaceutical composition according to claim 6, suitable for parenteral administration by subcutaneous (SC), intravenous (IV), intramuscular (IM), intradermal (ID), or intraperitoneal (IP) injection.

8. A long acting pharmaceutical composition comprising a therapeutically effective amount of the pentapolymer according to claim 1 in a depot form suitable for administration at a medically acceptable location in a subject in need thereof.

9. The long acting pharmaceutical composition according to claim 8, further comprising a pharmaceutically acceptable biodegradable or non-biodegradable carrier selected from PLGA, PLA, PGA, polycaprolactone, polyhydroxybutyrate, polyorthoesters, polyalkaneanhydrides, gelatin, collagen, oxidized cellulose, and polyphosphazene.

10. A method of treating an autoimmune disease comprising administering to a subject in need thereof an effective amount of the pentapolymer according to claim 1.

11. The method according to claim 10, wherein the autoimmune disease is multiple sclerosis.

12. The method according to claim 11, wherein the pentapolymer is administered to reduce the frequency of relapses in patients with Relapsing-Remitting Multiple Sclerosis (RRMS).

13. The method according to claim 10, wherein the pentapolymer is incorporated into a long lasting composition in a depot form suitable for administration at a medically acceptable location in the subject.

14. The method according to claim 10, comprising administering the pentapolymer in combination with at least one additional active agent.

* * * * *